United States Patent [19]

Guadagno et al.

[11] Patent Number: 4,582,685

[45] Date of Patent: Apr. 15, 1986

[54] TEST KIT FOR PERFORMING A MEDICAL TEST

[75] Inventors: Philip A. Guadagno; James R. Markus, both of Vidor, Tex.

[73] Assignee: Helena Laboratories Corporation, Beaumont, Tex.

[21] Appl. No.: 691,953

[22] Filed: Jan. 16, 1985

Related U.S. Application Data

[63] Continuation of Ser. No. 433,301, Oct. 7, 1982, Pat. No. 4,511,533.

[51] Int. Cl.⁴ .................. G01N 33/72; G01N 21/78
[52] U.S. Cl. .......................... 422/61; 206/205; 206/219; 422/56; 436/66; 436/165; 436/166; 436/904
[58] Field of Search ............... 422/61, 56, 58; 206/219, 205; 436/66, 165, 166, 904

[56] References Cited

U.S. PATENT DOCUMENTS

| | | |
|---|---|---|
| 2,350,239 | 5/1944 | Kohn . |
| 2,418,392 | 4/1947 | Bender . |
| 2,709,127 | 5/1955 | Grosskopf . |
| 2,838,377 | 6/1958 | Fonner ............................ 422/56 |
| 3,012,976 | 12/1961 | Adams et al. . |
| 3,036,894 | 5/1962 | Forestiere . |
| 3,175,558 | 3/1965 | Caillouette et al. . |
| 3,367,785 | 5/1968 | Finucane . |
| 3,406,015 | 10/1969 | Foster . |
| 3,446,596 | 5/1969 | Salivar et al. . |
| 3,572,997 | 3/1971 | Burk . |
| 3,666,421 | 5/1972 | Price . |
| 3,689,224 | 9/1972 | Agnew et al. . |
| 3,697,227 | 10/1972 | Goldstein et al. . |
| 3,770,383 | 11/1973 | Price . |
| 3,785,930 | 1/1974 | Ellis . |
| 3,986,834 | 10/1976 | Steinbrink, Jr. . |
| 3,990,850 | 11/1976 | Friedman et al. . |
| 4,106,478 | 8/1978 | Higashijima . |
| 4,110,079 | 8/1978 | Schaeffer et al. . |
| 4,175,923 | 11/1979 | Friend . |
| 4,195,056 | 3/1980 | Patel . |
| 4,371,374 | 2/1983 | Cerami et al. . |

Primary Examiner—Arnold Turk
Attorney, Agent, or Firm—Cullen, Sloman, Cantor, Grauer, Scott & Rutherford

[57] ABSTRACT

A test kit for preparing a chemical test pad used in testing for the presence of occult blood in a specimen. The test kit is a foil package enclosing an absorbant pad bearing a peroxygen agent and a solution of guaiac in alcohol in a separate packet or compartment from the absorbant pad. The separate packet or compartment being rupturable by applying hand pressure to the outside of the foil package to mix the peroxygen agent powder on the test pad and the guaiac solution prior to removing the absorbant pad from the foil package. The method relates to performing a medical test by activating a test pad bearing one reagent by applying another reagent thereto while remaining wholly within a protective foil package. According to the method a test pad containing the peroxygen agent is wetted with a solution of guaiac in alcohol prior to removal from the protective foil package and exposure to a specimen of fecal material and water in a test for occult blood.

1 Claim, 6 Drawing Figures

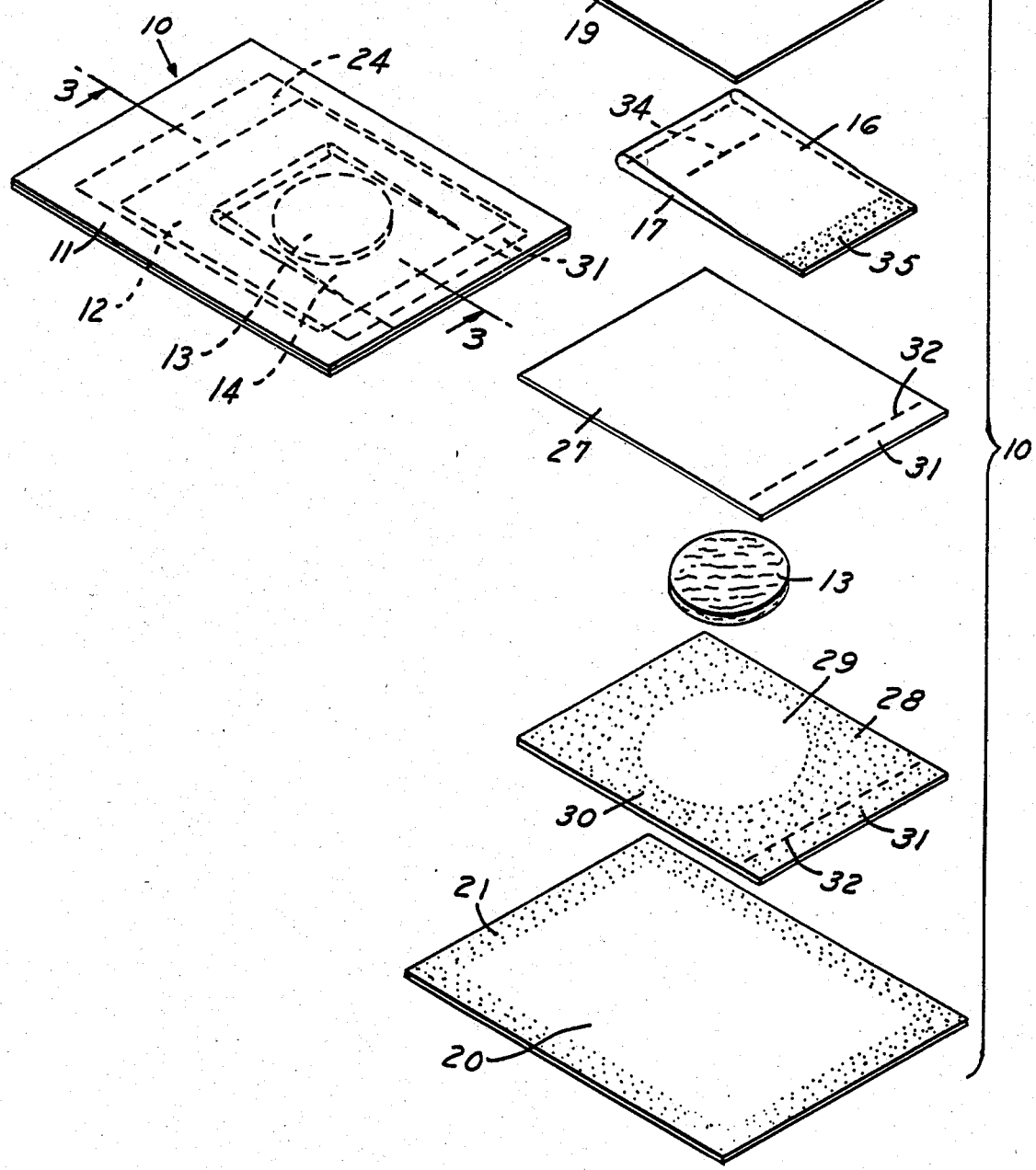

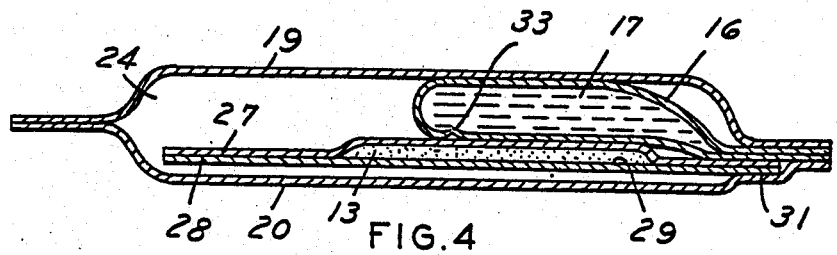
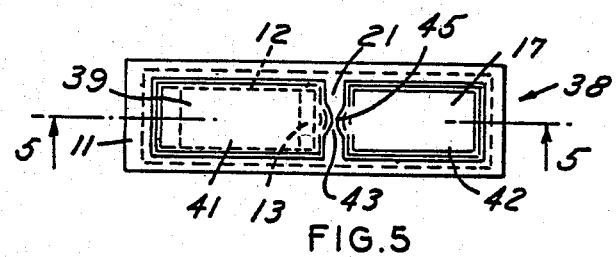
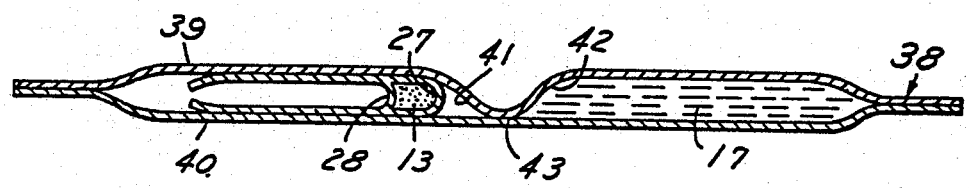
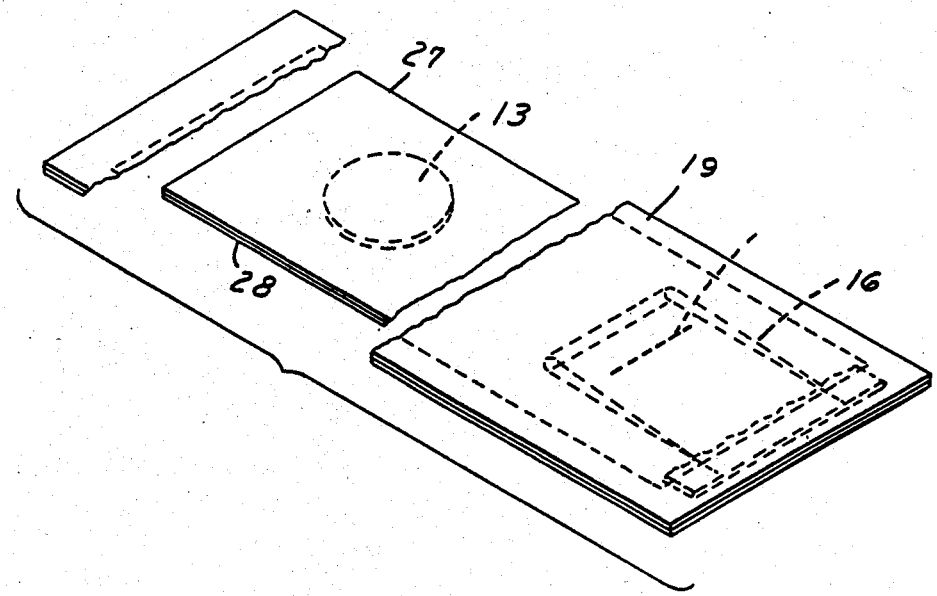

TEST KIT FOR PERFORMING A MEDICAL TEST

This application is a continuation of my U.S. patent application, Ser. No. 433,301, filed Oct. 7, 1982, now Pat. No. 4,511,533.

BACKGROUND OF THE INVENTION

1. Technical Field

The present invention relates to a test kit and a method for performing a medical test using a chemical test pad, and more particularly to a test kit and a method wherein two reagent materials used in a medical test are separately stored in a unitary package until ready for use.

2. Prior Art

Advances in medical science have led to the development of diagnostic tests for detecting various conditions. With many diseases it is imperative that early diagnosis be made so that treatment may be administered when most effective. Frequently, administration of the test and analysis of the test results are simple enough for patients to perform themselves. This is particularly true of tests using a sensitized swab or pad which changes color upon contact with a specimen. To assure acceptance by patients, self-administered tests must be as simple as possible to perform and analyze.

One type of diagnostic test, disclosed in U.S. Pat. No. 4,175,923 to Friend, is used to detect the presence of occult blood in fecal material. The presence of occult (not visible) blood is tested in a toilet bowl containing water and fecal material by first spraying a tissue which is impregnated with a guaiac reagent with a developing solution made up of alcohol and peroxide. The sensitized tissue is then placed in the toilet bowl to perform the test. If traces of blood are present in the toilet bowl, the guaiac reagent undergoes a reaction in which it turns blue.

The presence of occult blood in fecal material has been found to be an early sign of digestive tract cancer. It is important to detect the presence of blood before the blood from internal bleeding becomes visible in fecal material. If bleeding caused by digestive tract cancer is detected at an early stage, the changes of successful treatment are dramatically improved.

Since there is a natural aversion to handling fecal material it is preferable to test for the presence of occult blood in the toilet bowl. By so doing, many of the objections of patients to self-administering such a test are overcome. The test can be both performed and analyzed in the toilet bowl without direct contact with the fecal material thereby improving patient acceptance of the test.

However, the test disclosed in Friend suffers from certain drawbacks and problems. According to the test procedure described in the patent the subject must spray the guaiac impregnated paper with the alcohol and peroxide solution to activate the guaiac prior to performing the test. Many patients have been afraid to perform the test since they are required to handle a chemically treated paper and spray a chemical substance on the paper without fully understanding what it is they are dealing with. In performing the procedure the solution can be wasted or inadvertently sprayed on the patient or on objects other than the tissue. The peroxide solution is hazardous if it is sprayed in or otherwise comes in contact with a patient's eyes. The peroxide solution may also bleach some objects if accidentally spilled.

The present invention is directed to overcoming all of the prior objections to the method disclosed in Friend while still retaining all of the advantages of the test.

SUMMARY OF THE INVENTION

The invention relates to a self-contained test kit comprising a unitary package having two compartments, or separate zones, for storing two different reagents. The test kit is used by applying a force by hand to the outside of the unitary package to rupture a weakened portion of the seal or member which separates the two different reagents.

The test kit is a safe and sanitary device for combining chemical reagents. The test kit is ideal for self-administered medical tests requiring reagents to be mixed prior to performing the test. Since all mixing is performed inside the unitary package there is less chance that the reagents will be accidentally spilled. Also, patients having a fear, or lack of understanding, regarding chemicals will be less apprehensive since their contact with the reagents is minimized.

The present invention is described with reference to a test for occult blood in fecal material which is useful in preliminary diagnosis of digestive tract cancer. A peroxygen agent and a solution of guaiac in alcohol are the two reagents used in the invention. The reagents chosen are safe to use in a self-administered test. The safety of the test is increased since the peroxygen agent is contained within layers of an absorbant paper test pad.

Another feature of the present invention is that the weakened portion of the seal or member separating the two reagents is located to direct one reagent toward the other. This feature reduces the amount of reagent required and makes the kit less prone to accidental spillage of the reagents when the package is opened.

BRIEF DESCRIPTION OF THE DRAWINGS

A better understanding of the invention can be obtained by reading the following specification in conjunction with the accompanying drawings, wherein:

FIG. 1 is a perspective view of the test kit of the present invention showing the relation of the various parts with hidden parts being shown with dotted lines.

FIG. 2 is an exploded perspective view of the embodiment of the invention shown in FIG. 1.

FIG. 3 is a longitudinal cross-section taken along the line 3—3 in FIG. 1.

FIG. 4 is a plan view of another embodiment of the invention.

FIG. 5 is a longitudinal cross-section of the embodiment of the invention shown in FIG. 4.

FIG. 6 is a perspective view of the embodiment of the invention shown in FIG. 1 with the package opened and the test pad separated from the package.

DETAILED DESCRIPTION OF THE INVENTION

Referring now to FIGS. 1 through 3, the test kit is generally indicated by the reference numeral 10. The test kit 10 includes an outer package 11 which is a rectangular foil member enclosing a test pad 12 containing a first reagent 13. A packet 16 containing a liquid reagent 17 is also enclosed within the outer package 11. The packet 16 is adapted to be ruptured, or broken, for the purpose of allowing the second reagent 17 to contact the first reagent 13 to activate the first reagent prior to performing a medical test.

The test kit is particularly well-suited to perform a test for determining the presence of occult blood in fecal material. According to the present invention, such a test may be performed by using potassium hydrogen peroxymonosulfate, which is a monopersulfate compound sold by DuPont under the trademark Oxone, as the first reagent 13 and a solution of guaiac in alcohol as the second reagent 17. The peroxygen agent is retained in place within the test pad 12. This harmless solution of guaiac in alcohol is activated only after combining with the peroxygen agent. All of the reagents necessary to perform the test are contained within the outer package 11 and all preparation takes place within the protection of the outer package 11. Thus, patient contact with the reagent products is kept to an absolute minimum.

The outer package 11 is provided to protect the reagent materials from moisture during storage. The outer package 11 includes top foil sheet 19 and bottom foil sheet 20 which are each sealed together by means of a heat bonding adhesive 21 which is deposited about the periphery of the foil sheets. When the top and bottom foil sheets are bonded together, a closed pocket 24 is formed therebetween for containing all of the materials necessary to perform the test.

The test pad 12 includes a top layer 27 of absorbant material that is permeable by alcohol or water based reagents. In a preferred embodiment, the absorbant material of the top layer is paper. The bottom layer 28 is made of a durable paper product or cellulosic material which is biodegradable but will support the top layer 27 when wet to prevent the test pad 12 from tearing. The top and bottom layers 27 and 28 sandwich the first reagent 13 therebetween in a containment pocket 29. To facilitate observation of the color change the top and/or bottom layers 27 and 28 are preferably translucent when wet. The top and bottom layers 27 and 28 are cemented together about their periphery by an adhesive 30 or suitable mechanical seals.

The test pad 12 is intended to be removed from the outer package 11 to perform the test. However, if the test pad 12 is small enough to move within the enclosed pocket 24 it may be desirable to anchor a small portion 31 or tab of the test pad 12 between the top and bottom foil sheets 19 and 20. If desired, the test pad 12 may include a perforated line 32 so that the test pad 12 will be easy to remove from the outer package 11.

The packet 16 contains the second or liquid reagent 17, which is a guaiac in alcohol reagent solution. A weakened portion 33 of the packet 16 is formed by forming a score line 34 on the packet 16 in an area proximate the first reagent 13 on the test pad 12. The weakened portion 33 is provided to assure that the packet 16 is easily rupturable when the outer package 11 is squeezed or impacted by a patient's hands. The score line 34 allows the packet to rupture, or tear, in a predetermined localized area which preferably directs the liquid reagent 17 toward the first reagent 13 on the test pad 12. An anchoring end 35 of the packet 16 is firmly secured between the top and bottom foil sheets 19 and 20 so that the packet 16 remains with the outer package 11 when the test pad 12 is removed from the outer package 11.

The reagent chemicals used to detect the presence of occult blood in a specimen according to the present invention are safe for a patient to self-administer. Traditional tests for occult blood recommended the use of a tissue impregnated with guaiac reagent that was activated by spraying with a peroxide solution. The peroxide solution is somewhat hazardous and can cause injury if it is introduced into a person's eye or can bleach clothing or other objects upon contact therewith. The possibility of an accidental injury or damage to clothing or other objects is increased when the peroxide solution is sprayed, uncontained, on the test pad. However, since the peroxygen agent used in the present invention is in powder form and is sandwiched between layers of the pad the chance of injury is minimized. The solution of guaiac in alcohol is harmless. Since all mixing of the reagents takes place within the package 11, contact with the reagents is avoided making the present invention much safer to self administer than prior test procedures.

Another embodiment of the invention is shown in FIGS. 4 and 5, wherein the outer package 38 includes a top foil sheet 39 and a bottom foil sheet 40 secured together about their periphery by means of a heat seal adhesive, as previously described. The package 38 is divided into first and second compartments 41 and 42 by an internal seal 43. The first reagent 13 is retained between two layers 27 and 28 in the center of the test pad 12. The test pad 12 is disposed in the first compartment 41 and is doubled over to place the first reagent 13 in close proximity to the internal seal 43.

As shown in FIG. 4, a weakened portion 45 is preferably formed in the middle of the internal seal 43 to cause the seal to rupture when pressure is applied to the exterior of the second compartment 42. The weakened portion 45 is provided by reducing width of the seal by reducing the amount of adhesive 21 between the top and bottom foil sheets 39 and 40 in a specified area. By centrally locating the weakened portion 45 the liquid reagent 17 in the second compartment 42 will be directed to the center of the first compartment 41 when the internal seal 43 ruptures. The liquid reagent 17 is then squirted directly onto the portion of the test pad 12 bearing the first reagent 13. Since the second reagent 17 is directed toward the first reagent, the amount of liquid reagent necessary to wet the first reagent 13 is reduced and the remainder of the test pad 12 may remain substantially dry. As a result, the patient is not exposed to excess solution when performing the test. In addition to being less objectionable to a user, the amount of the second reagent used is minimized which reduces the cost of the test kit 10.

The method of using the test kit 10 is described with reference to FIGS. 3 through 6. When it is necessary to perform the test for which the test kit 10 is designed, the outer package 11 is squeezed or impacted by hand pressure to burst the packet 16 at the weakened portion 33 in the embodiment of FIG. 6. Alternatively, in the test kit shown in FIGS. 4 and 5, hand pressure is applied to the outside of the second compartment 42 to rupture or break the internal seal 43 at the weakened portion 45. In both forms of the test kit, the second reagent 17 flows toward the test pad 12 and is absorbed through the absorbant top layer 27 of the test pad 12 to activate the first reagent 13. The patient then tears open the outer package 11 on one end to remove the wetted test pad 12 from the outer package 11. The test pad is then exposed to the test specimen.

In tests for occult blood in fecal material, the pad is thrown into the toilet bowl containing the fecal material and water. If the guaiac solution and peroxygen agent on the test pad 12 changes color, the test is positive and further clinical tests may be performed to determine the cause of the occult blood in the specimen. If the test pad 12 does not change color after a sufficient period of time, the test is negative and absence of occult blood in the specimen can be assumed. The test pad 12 can then be flushed with the specimen from the toilet bowl without a need to further handle the test pad 12.

The invention has been described so as to enable one skilled in the art to make and practice the invention in reference to two types of test kit and a method for preparing the test device. It should be understood that the above description may be modified in many respects without departing from the scope of the invention. The above detailed description should be read as being exemplary and not in a limiting sense.

Having fully described two operative embodiments of the invention, I now claim:

1. A test kit for determining the presence of occult blood in fecal material comprising:

a package having a top foil sheet and a bottom foil sheet joined together about peripherial portions thereof by a heat seal adhesive to form a closed pocket therebetween; a rupturable intermediate internal seal between said foil sheets extending from one side of said package to the opposite side thereof and dividing said pocket into first and second compartments of generally the same size;

an absorbant test pad removeably disposed within said first compartment having a first reagent retained within said absorbant pad, said absorbant pad comprising a first layer of absorbant material being permeable to alcohol or water, and a second layer of cellulosic material for defining with said first layer a containment pocket, said first reagent being a peroxygen agent consisting of potassium hydrogen peroxymonosulfate disposed in said containment pocket; said test pad being folded over upon itself and placed in said first compartment with the first layer of said absorbant test pad and said first reagent being located directly opposite from said rupturable internal seal;

a second liquid reagent comprising a solution of guaiac in alcohol disposed in and completely occupying said second compartment;

said rupturable internal seal having a weakened portion in the middle of said internal seal adapted to be ruptured to allow the second liquid reagent to contact the first reagent for activating the absorbant test pad, said rupturable internal seal being ruptured when hand pressure is applied to the package, with said solution of guaiac and alcohol being absorbed through said first layer of the absorbant test pad to activate the peroxygen agent in the containment pocket of said pad prior to performing a test using said absorbant pad.

* * * * *

UNITED STATES PATENT OFFICE
CERTIFICATE OF CORRECTION

Patent No. 4,582,685　　　　　　　　　Dated April 15, 1986

Inventor(s) Guadagno et al

It is certified that error appears in the above-identified patent and that said Letters Patent are hereby corrected as shown below:

> In the cover page (first page), reference to Inventors, delete "James R. Markus" and insert —James R. M. Sanford—.

Signed and Sealed this

Ninth Day of December, 1986

*Attest:*

DONALD J. QUIGG

*Attesting Officer*　　　　*Commissioner of Patents and Trademarks*